United States Patent [19]

Stefanoff

[11] 4,085,514
[45] Apr. 25, 1978

[54] PARALLEL WALL INDICATOR

[76] Inventor: Boris T. Stefanoff, 16039-132nd Pl. SE., Renton, Wash. 98055

[21] Appl. No.: 631,994

[22] Filed: Nov. 14, 1975

[51] Int. Cl.² .................... G01B 3/56; G01C 9/12; A61C 3/00
[52] U.S. Cl. .................... 33/343; 32/40 R; 33/1 N; 33/174 D; 33/349
[58] Field of Search .............. 33/1 N, 174 D, 174 E, 33/333, 334, 341, 343, 349, 399, 400, 401; 32/40 R

[56] References Cited
U.S. PATENT DOCUMENTS

| 1,186,394 | 6/1916 | Hamilton | 33/349 |
| 1,451,507 | 4/1923 | Harris et al. | 32/40 R |
| 1,972,122 | 9/1934 | Woodyard | 33/343 |
| 3,047,957 | 8/1962 | Conway | 33/343 |
| 3,845,565 | 11/1974 | Newswanger | 33/1 N |

FOREIGN PATENT DOCUMENTS 1,198 of 1872 United Kingdom ................ 33/343

Primary Examiner—Richard E. Aegerter
Assistant Examiner—Richard R. Stearns
Attorney, Agent, or Firm—Dowrey & Cross

[57] ABSTRACT

The indicator includes rotationally movable indicator means for indicating a selected reference angle and pendulum actuator means for maintaining the angular position of the indicator means substantially constant with respect to vertical. The indicator is particularly suited for use in the correlated preparation of multiple teeth for application of one piece multiple crown castings by forming corresponding inclined teeth surfaces parallel.

11 Claims, 7 Drawing Figures

PARALLEL WALL INDICATOR

BACKGROUND OF THE INVENTION

This invention relates to geometric instruments, one particular application of which relates to dental instruments for and methods of preparing one or more teeth for application of a crown or bridge.

In the preparation of crowns or copings; it is essential that each crown or coping fit precisely to the margin of the prepared tooth surfaces. Otherwise, it is not possible to achieve a tight margin seal so that food particles, acids, etc., are allowed to accumulate underneath the crown and destroy the tooth. The tooth misial and distal surfaces as well as the buccal, labial and lingual surfaces, as the case may be, are prepared by grinding them on an incline (desirably 6° to the vertical) to form a tapered prepared tooth configuration suitable for preparation of a wax pattern and subsequent reception of the crown or coping. Inasmuch as this grinding process is presently done by eye, however, the prepared tooth surfaces often tend to be of non-uniform shape, include undercut portions, and generally fail to provide, on a consistent basis, a prepared tooth configuration suitable for accurate preparation of the wax pattern, the non-uniform undercut portions tending to distort the wax pattern during removal thereof from a die. (The die is formed by a plaster model taken from a wax impression of the prepared teeth). In many practical cases, therefore, the crown or bridge prepared from the wax pattern does not fit precisely and must be fitted by acutally grinding it, or one or more teeth, until it can be forced into position, with resultant damage to or even destruction of a precise margin fit.

In the preparation and fitting of individual crowns, the process mentioned above generally is acceptable because each tooth is prepared and fitted with a crown independently so that the effects of inaccurately prepared tooth surfaces are reflected in the preparation and fitting of only one crown. This is not the case with dental bridges, especially bridges formed as one piece multiple crown castings, because the bridge must be prepared and fitted so that all its crowns fit precisely to the margins of several adjacent teeth, or to abutments separated by a ponic, simultaneously. Heretofore, the preparation and fitting of bridges have been done in much the same manner as the preparation and fitting of individual crowns—the crowns making up the bridge being formed independently and soldered together. Soldering, however, tends to distort the alignment of the individual crowns and is time consuming. Although one piece multiple castings now offer a means for eliminating soldering to obtain accurate alignment (and hence fit) of the individual crowns and increasing productivity, the independently prepared teeth almost invariably include sufficient non-uniformities that an accurate wax pattern is exceedingly difficult to obtain. Consequently, one piece multiple castings prepared from such wax patterns often necessitate as much or more alteration to make them fit than soldered bridges—the margin seals obtained with both types of bridges being unreliable in many instances.

SUMMARY OF THE INVENTION

This invention provides a method and apparatus with which the preparation of two or more teeth may be correlated to achieve accuracy and consistency in the configuration thereof and in this way minimize or substantially eliminate distortion in the wax patterns prepared therefrom. According to the principles of this invention, the preparation of teeth surfaces may now be performed in an accurate, consistent manner by forming corresponding prepared teeth surfaces parallel. Using this invention, therefore, one piece multiple crown castings may be prepared and fitted in a highly effective and economical manner to achieve reliable margin seals.

According to one preferred embodiment of the invention for dental instrument application, movable indicator means for indicating a selected reference angle of inclination of corresponding teeth surfaces are maintained at a desired angular position with respect to vertical by pendulum actuator means. The indicator means are set to indicate a selected reference angle and are positioned adjacent successive corresponding prepared teeth surfaces. At each prepared tooth surface, the selected reference angle is compared with the angle of inclination thereof, and an appropriate modification is made to the prepared tooth surface until it corresponds to the selected reference angle. Thus, all corresponding teeth surfaces may be formed parallel in a consistent, accurate manner. The dental instrument is equally adaptable for correlating the preparation of upper and lower teeth.

Thus, it will be appreciated from the foregoing summary that this invention positively assures accuracy and consistency in most bridge preparations, especially one piece multiple castings, with concomitant reduction in time and effort needed to actually fit the prepared bridge, the latter substantially increasing dentist productivity and minimizing patient discomfort. The principles of this invention, of course, are further applicable to the preparation and fitting of individual crowns, the indicator in this instance providing a convenient straight line reference to aid in the formation of flat surfaces devoid of undercutting.

These and other features, objects and advantages of the present invention will become apparent in the detailed description and claims to follow taken in conjunction with the accompanying drawings in which:

DETAILED DESCRIPTION OF THE DRAWINGS

Figure 1:
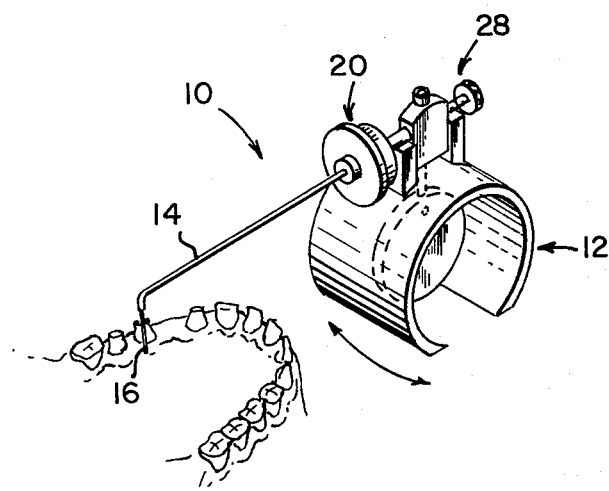
FIG. 1 is a perspective view of the dental instrument of this invention.
Figure 2:
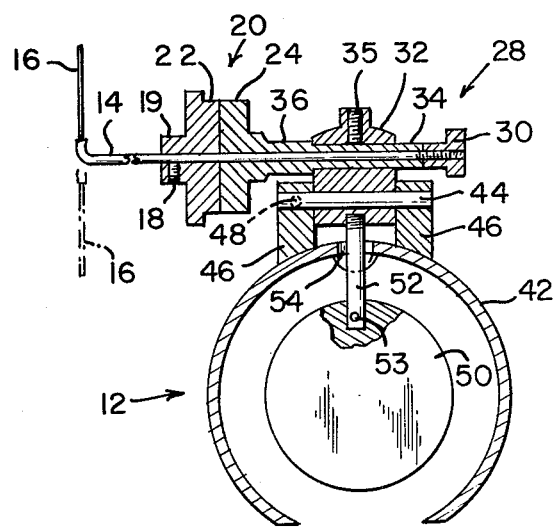
FIG. 2 is a longitudinal vertical section of the FIG. 1 instrument.
Figure 3:
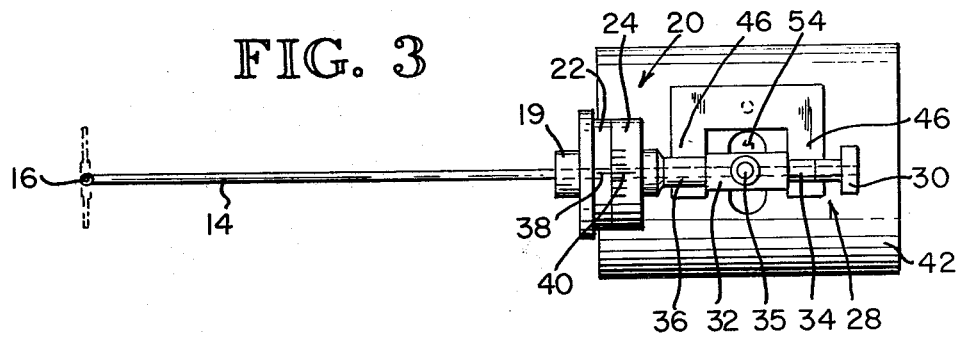
FIG. 3 is a top plan view of the FIG. 1 instrument.

The dental instrument of FIGS. 1–3 includes an indicator assembly 10 and an actuator assembly 12. The illustrated instrument is of light weight, compact construction suitable for hand-held usage with little or no required maintenance. The instrument preferably is formed of material capable of withstanding appropriate sterilization procedures, such as autoclaving, without suffering detrimental effects.

The indicator assembly 10 of FIGS. 1–3 includes an elongated member 14, which terminates at one end in a perpendicular reference angle indicator portion 16 of reduced cross sectional and rectilinear configuration. Portion 16 could be pointed or coated with appropriate colored material to suit specific applications. FIG. 1 illustrates the general orientation of the instrument and portion 16 to correlate preparation of three abutments (the tapered teeth), two of which are separated by a ponic (not shown). The correlation procedure will be described presently but with reference to uppers (see FIGS. 4–7).

The indicator assembly 10 of FIGS. 1–3 further includes an adjustment assembly 28 for selectively adjusting and maintaining the angular position of portion 16 with respect to assembly 12, and a guage assembly 20 for representing the selected angular position of portion 16 in appropriate increments. Assembly 28 mounts member 14 (and hence portion 16) for selective rotational movement about the longitudinal axis of member 14 with respect to a block 32 pivotally mounted by the assembly 12, both presently to be described in detail. Assembly 28 includes an elongated hollow shaft having two cylindrical spacer portions 34 and 36, the enlarged diameter spacer portion 36 engaging and being positioned by block 32 and smaller diameter spacer portion 34 extending therethrough, as shown (FIG. 2). Shaft spacer portion 34 is fixed with respect to block 32 by a set screw 35 or other means. Member 14 extends axially through spacer portions 34 and 36, and is threadably engaged at its other end with an adjustment screw 30 which bears against spacer portion 34. Assembly 28 further includes a cylindrical clamping portion 19 located at the end thereof opposite screw 30 and fixed to member 14 by set screw 18 or other means. Screw 30, therefore, when tightened, exerts an axial force upon member 14, which transmits and applies such force via portion 19 to the remaining components of assembly 28, thereby bringing their opposed faces into frictional engagement and fixing the relative angular positions thereof. When loosened, member 14 and portion 19 are free to rotate relative to portions 34 and 36 and block 32. Thus, it is possible, by selectively loosening screw 30, rotating portion 16 to a desired angular position as depicted by broken line positions in FIG. 3, and then tightening screw 30, to selectively adjust and maintain the angular position of portion 16 with respect to block 32. In the adjusted fixed condition, portion 16, member 14, the components of assembly 28 and block 32 may pivot as a unit under the control of assembly 12, presently to be described.

Assembly 20 is located adjacent the left illustrated end of assembly 28, leaving a major portion of member 14 for insertion into the mouth (see FIG. 1). Assembly 20 includes two adjacent disc shaped angle gauges 22 and 24 respectively integral with, or secured to portions 19 and 36. Gauges 22 and 24 surround and are rotatable relative to one another with respect to the longitudinal axis of member 14. The angular position of gauge 22 with respect to gauge 24 is adjustable simultaneously with, and in a generally similar manner to adjustment of portion 16, gauge 22 rotating conjointly with member 14 relative to gauge 24. Thus gauge 22 reflects the actual or true angular position of portion 16 with respect to gauge 24 (and hence to block 32 and actuator 12).

Referring to FIG. 3, gauge 22 is provided with a single hash mark 38 and gauge 24 is provided with a set of parallel hash marks 40. Hash mark 38, when lined up with one hash mark 40, represents the actual position or set angle of portion 16, hash marks 40 being spaced apart at appropraite intervals (e.g. 6°) corresponding to the range of selected angular positions of portion 16. Additional or other suitable indicia in place of the illustrated hash marks, of course, could be provided, if desired. Still referring to FIG. 3, it will be evident that the hash marks 40 further may represent the direction of adjustment of portion 16, hash marks to the right of the median hash mark (the central and longest of hash marks 40) reflecting adjustment of the portion to the right of true vertical, and vice versa. Thus, by adjusting hash mark 38 to the left or right of the median, it is possible to automatically adjust portion 16 to indicate inclinations of oppositely inclined surfaces (e.g. the misial and distal surfaces of FIGS. 4–7). Further, a second generally similar set of hash marks 38 and 40 may be provided at diametrically opposed locations on gauges 22 and 24 to allow portion 16 to be rotated 180° and adjusted selectively for correlation of the lower or upper teeth as desired. FIG. 1 illustrates portion 16 in position for correlation of the lowers, whereas FIGS. 2 and 3 illustrate portion 16 in position for correlation of the uppers (portion 16 pointing downward in FIG. 1 and upward in FIGS. 2 and 3), In both cases, the opposed sets of hash marks 38 and 40 provide the necessary representation of the angular position of portion 16 with respect to vertical. To aid in turning screw 30, or gauge 22, portions of the peripheral surfaces of either, or both, may be roughened.

The actuator assembly 12 of FIGS. 1–3, includes a housing 42 for pivotally supporting block 32 to swing about an axis defined by pivot shaft 44 spaced from and parallel to the longitudinal axis of member 14. A generally U-shaped support block 46 upstanding from the upper surface of housing 42 mounts shaft 44, as shown. Shaft 44 is fixed with respect to block 46 and housing 42 by a set screw 48 or other appropriate means. The actuator assembly 12 further includes a disc shaped mass or pendulum 50 which depends via arm 52 from block 32. Arm 52 extends through an elongated opening 54 in the top of housing 42 and is threadably engaged at its upper end to block 32. The lower end of arm 52 is secured by set screw 53 or other means to pendulum 50. The pendulum 50 is arranged to face in a direction perpendicular to the pivot axis defined by shaft 44 in order to swing about that pivot axis as indicated by arrows in FIG. 1, thereby causing the portion 16 to swing correspondingly. Thus, it will be appreciated that portion 16 will be maintained in or continuously returned to a fixed position with respect to vertical under the influence of pendulum 50, despite variations in attitude of housing 42. It is possible, therefore, by adjusting the angular position of portion 16 with respect to block 32, and hence with respect to pendulum 50, using the adjustment assembly 28 described previously, to select the angular position of portion 16 with respect to vertical and maintain it substantially constant at all times, thereby providing a selected angle reference which remains substantially constant with respect to vertical, despite changes in attitude of housing 42.

Housing 42 further serves to provide a handle which may be gripped manually during operation and use of the instrument. To this end, housing 42 is of generally inverted C-shape cross section and substantially surrounds pendulum 50 to allow free swinging movement thereof. Housing 42 preferably is of sufficient length to provide an appropriate manual gripping surface.

Figure 4:
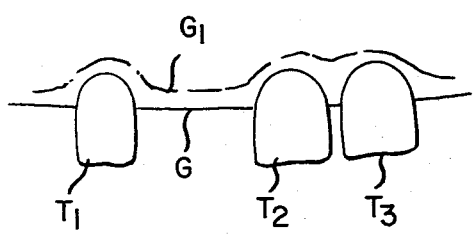
FIGS. 4–7 are schematics depicting operation of the FIG. 1 instrument.
Figure 5:
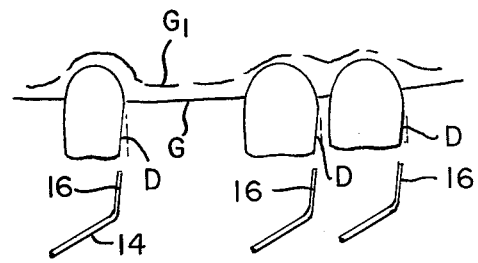
Figure 6:
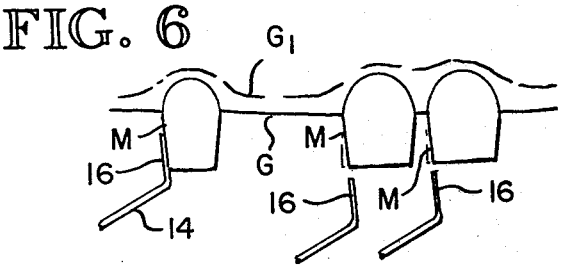

Referring now in particular to FIGS. 4–7, the operation of the instrument of FIGS. 1–3 and the method of this invention for correlating corresponding surfaces of prepared teeth for application of a bridge will now be described. FIGS. 4–7 depict a typical preparation sequence, in this case with respect to three upper teeth $T_1$, $T_2$, and $T_3$—the tooth intervening between teeth $T_1$ and $T_2$ having been removed previously. The gingiva or gum tissue is indicated by solid line designated G in the condition subsequent to extraction of the missing tooth and by broken line $G_1$ as it would appear subsequent to application of a bridge. FIG. 4 represents teeth $T_1$ $T_2$ and $T_3$ as they would appear initially. Partial preparation of these teeth (in this case the distal D and misial M surfaces, respectively) is depicted in FIGS. 5 and 6. The initial grinds to form these prepared surfaces may be done by eye; however, to ensure accurate and consistent formation of the prepared teeth, especially in preparation for application of one piece multiple crown castings, preparation of each individual tooth is correlated to preparation of the remaining teeth by forming corresponding surfaces thereof parallel.

Figure 7:
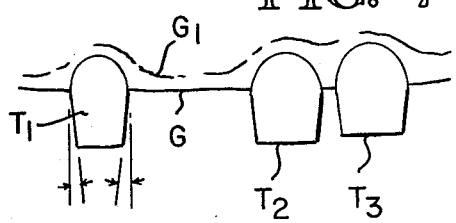

Correlation of two opposed sets of corresponding surfaces (in this case the distal D and misial M surfaces, respectively) is depicted in FIGS. 5 and 6. The instrument of FIGS. 1-3 is positioned with portion 16 successively adjacent corresponding prepared teeth surfaces D and M, portion 16 being set at a selected angular position (e.g. 6°), from vertical, as shown previously. At each illustrated position of the portion 16, the reference angle of inclination represented thereby is compared with the angle of inclination of the partially prepared tooth surface. Each tooth surface thereafter may be modified by further grinding as necessary to conform the angle of inclination thereof with the reference angle represented by the portion 16. Inasmuch as the reference angle represented by the portion 16 remains constant with respect to vertical at each illustrated position thereof by virtue of the pendulum actuator previously described, it is possible to achieve substantial parallelism between corresponding teeth surfaces. The completed teeth preparation in which corresponding teeth surfaces are parallel is depicted in FIG. 7. This correlation process is repeated with the remaining teeth surfaces to be prepared, in this case, the lingual and buccal surfaces (see FIG. 1). The corresponding teeth surfaces thus formed allow the preparation and fitting of individual crowns, one piece multiple castings (in this case the casting being made up of three abutment castings and a ponic), or preparation for full mouth reconstruction. It will be understood, of course, that the illustrated rectilinear construction of portion 16 also provides a straight line reference to aid in the formation of flat tooth surfaces, devoid of undercutting.

During the foregoing preparation procedure, the patient is positioned in an upright position with his or her head maintained in a vertical position. Thus, the dental instrument of this invention may be moved and positioned adjacent appropriate teeth surfaces by hand—the reference angle indication remaining constant with respect to vertical—without the inconvenience of head mountings (e.g., headbands, bite attachments, etc.), or complex articulated arm supports, both of which are employed in the positioning of prior measurement instruments and apparatus for dental application in general.

While the preferred embodiment of the invention has been illustrated and described herein, variations will become apparent to one of ordinary skill in the art. Accordingly, the invention is not to be limited to the specific embodiment illustrated and described herein and the true scope and spirit of the invention are to be determined by reference to the appended claims.

The embodiments of the invention in which an exclusive property or privilege is claimed are defined as follows:

1. A dental instrument, comprising:
   indicator means including an elongated portion of length sufficient to be insertable into a mouth with one end portion thereof adjacent a prepared tooth, and a pointer portion projecting from said one end portion for indicating a reference line;
   pendulum means movable with respect to a rest position about a pivot axis parallel to the longitudinal axis of said elongated portion; and
   connector means for connecting the other end portion of said elongated portion with said pendulum means such that said pointer portion will be positioned at a predetermined angular position with respect to vertical when said pendulum means assume said rest position during successive comparisons of the angular disposition of said reference line with the angles of inclination of corresponding prepared teeth surfaces.

2. The instrument of claim 1, wherein said connector means are further operative for permitting selective rotational movement of said pointer portion with respect to said pendulum means about the longitudinal axis of said elongated portion in order to selectively adjust the angular position at which said pointer portion will be positioned when said pendulum means assume said rest position.

3. The instrument of claim 2, wherein said connector means include elongated spacer means slidably engaging said other end portion and secured to said pendulum means, means engaged with said other end portion for selectively applying a force to one end of said spacer means in a direction toward said one end portion, and stop means secured to said elongated portion adjacent said other end portion for engaging the other end of said spacer means and preventing rotational movement of said elongated portion about its longitudinal axis with respect to said spacer means during application of said force.

4. The instrument of claim 2, further comprising means mounted by said connector means for indicating a selected angular position of said pointer portion with respect to vertical.

5. The instrument of claim 1, wherein said pivot axis is spaced from the longitudinal axis of said elongated member and parallel thereto.

6. The instrument of claim 1, wherein said pendulum means include a hollow handle member, a mass, and means secured to said connector means and upstanding from said handle member for pivotally supporting said mass to swing in said handle member about said pivot axis in a direction perpendicular to the longitudinal axis of said elongated portion.

7. A dental instrument, comprising:
   indicator means including an elongated portion of length sufficient to be insertable into a mouth with one end portion thereof adjacent a prepared tooth, and a pointer portion projecting from said one end portion for indicating a reference line;
   pendulum means movable with repsect to a rest position about a pivot axis parallel to the longitudinal axis of said elongated portion; and
   connector means for (1)connecting the other end portion of said elongated portion with said pendulum means such that said pointer portion will be positioned at a predetermined angular position with respect to vertical when said pendulum means assume said rest position during successive comparisions of the angular disposition of said reference line with the angles of inclination of corresponding prepared teeth surfaces, and (2) permitting selective rotational movement of said pointer portion with respect to said pendulum means about the longitudinal axis of said elongated portion in order to selectively adjust the angular position at which said pointer portion will be positioned when said pendulum means assume said rest position;

said pendulum means including a hollow handle member, a mass, and pivot means secured to said connector means and upstanding from said handle member for pivotally supporting said mass to swing in said handle member about said pivot axis in a direction perpendicular to the longitudinal axis of said elongated portion;

said connector means including elongated spacer means slidably engaging said other end portion and secured to said pivot means, means engaged with said other end portion for selectively applying a force to one end of said spacer means in a direction toward said one end portion, and stop means secured to said elongated portion adjacent said other end portion for engaging the other end of said spacer means and preventing rotational movement of said elongated portion about its longitudinal axis with respect to said spacer means during application of said force.

8. In a geometric instrument including pendulum means, and a pointer positionable by said pendulum means at an angular position with respect to vertical when said pendulum means assume a rest position, the improvement comprising:

connector means connected to said pendulum means and said pointer for permitting selective movement of said pointer with respect to said pendulum means in order to selectively adjust the angular position at which said pointer will be positioned when said pendulum means assume said rest position;

said pointer including an elongated portion and a pointer portion projecting from one end portion of said elongated portion;

said pendulum means including a hollow handle member, a mass, and means secured to said connector means and upstanding from said handle member for pivotally supporting said mass to swing in said handle member about a pivot axis parallel to the longitudinal axis of said elongated portion in a direction perpendicular to the longitudinal axis thereof;

said connector means including elongated spacer means slidably engaging the other end portion of said elongated member and secured to said pendulum means, means engaged with said other end portion for selectively applying a force to one end of said spacer means in a direction toward said one end portion, and stop means secured to said elongated portion adjacent said other end portion for engaging the other end of said spacer means and preventing rotational movement of said elongated portion about its longitudinal axis with respect to said spacer means during application of said force.

9. In a geometric instrument including pendulum means, and a pointer positionable by said pendulum means at an angular position with respect to vertical when said pendulum means assume a rest position, the improvement comprising:

connector means connected to said pendulum means and said pointer for permitting selective movement of said pointer with respect to said pendulum means in order to selectively adjust the angular position at which said pointer will be positioned when said pendulum means assume said rest position;

said pointer including an elongated portion and a pointer portion projecting from one end portion of said elongated portion;

said connector means including elongated spacer means slidably engaging the other end portion of said elongated portion and secured to said pendulum means, means engaged with said other end portion for selectively applying a force to one end of said spacer means in a direction toward said one end portion, and stop means secured to said elongated portion adjacent said other end portion for engaging the other end of said spacer means and preventing rotational movement of said elongated portion about its longitudinal axis with respect to said spacer means during application of said force.

10. In a geometric instrument including pendulum means, and a pointer positionable by said pendulum means at an angular position with respect to vertical when said pendulum means assume a rest position, the improvement comprising:

connector means connected to said pendulum means and said pointer for permitting selective movement of said pointer with respect to said pendulum means in order to selectively adjust the angular position at which said pointer will be positioned when said pendulum means assume said rest position;

said pointer including an elongated portion and a pointer portion projecting from said elongated portion;

said pendulum means swinging about a pivot axis spaced from the longitudinal axis of said elongated portion and parallel thereto.

11. In a geomertric instrument including pendulum means, and a pointer positionable by said pendulum means at an angular position with respect to vertical when said pendulum means assume a rest position, the improvement comprising:

connector means connected to said pendulum means and said pointer for permitting selective movement of said pointer with respect to said pendulum means in order to selectively adjust the angular position at which said pointer will be positioned when said pendulum means assume said rest position;

said pointer including an elongated portion and a pointer portion projecting from said elongated portion;

said pendulum means swinging about a pivot axis parallel to the longitudinal axis of said elongated portion, and including a hollow handle member, a mass, and means secured to said connector means and upstanding from said handle member for pivotally supporting said mass to swing in said handle member about said pivot axis in a direction perpendicular to the longitudinal axis of said elongated portion.

* * * * *